United States Patent
Oya et al.

(10) Patent No.: US 6,323,038 B1
(45) Date of Patent: Nov. 27, 2001

(54) DIAGNOSTIC REAGENT FOR COMPLICATIONS ASSOCIATED WITH DIABETES OR RENAL FAILURE

(75) Inventors: Tomoko Oya, Aichi; Hiroyuki Kobayashi, Tokyo; Mitsuo Akiba, Tokyo; Norihiro Kakimoto, Tokyo; Yasujiro Morimitsu, Tokyo; Toshihiko Osawa, Aichi, all of (JP)

(73) Assignee: Asai Germanium Research Institute Co., Ltd., Kanagawa (JP)

( * ) Notice: Subject to any disclaimer, the term of this patent is extended or adjusted under 35 U.S.C. 154(b) by 0 days.

(21) Appl. No.: 09/482,927

(22) Filed: Jan. 14, 2000

Related U.S. Application Data

(63) Continuation of application No. PCT/JP98/03190, filed on Jul. 16, 1998.

(30) Foreign Application Priority Data

Jul. 18, 1997 (JP) .................................... 9-209804

(51) Int. Cl.$^7$ ............................ G01N 21/75; A01N 43/48
(52) U.S. Cl. .................. 436/166; 436/811; 436/106; 436/119; 436/127; 422/61; 546/296; 546/114; 546/261; 546/273.7; 546/290; 546/297; 546/301; 546/304; 514/277; 514/279; 514/299; 514/300; 514/301; 514/315; 514/317; 514/327
(58) Field of Search ................... 546/296, 114, 546/261, 273.7, 290, 297, 301, 304; 514/277, 279, 299, 300, 301, 315, 317, 327; 436/811, 106, 119, 127, 166; 422/61

(56) References Cited

U.S. PATENT DOCUMENTS 3,530,138 * 9/1970 Undheim et al. .................. 260/294.8
5,374,712 12/1994 Monnier et al. .................... 536/17.3

FOREIGN PATENT DOCUMENTS 06-73057 A 3/1994 (JP) .
WO 97/07803 3/1997 (WO) .

* cited by examiner

Primary Examiner—Jill Warden
Assistant Examiner—Monique T. Cole
(74) Attorney, Agent, or Firm—Kubovcik & Kubovcik

(57) ABSTRACT

In view of the situation of the prior art, the present invention specifies the structure of a late-stage product of Mailard reaction in vivo having a close relation with various tissue disorders, and provides a diagnostic reagent for complications associated with diabetes or renal failure, containing the above compound as a main component. The diagnostic reagent of the present invention for complications associated with diabetes or renal failure contains a pyridinium compound represented by the following formula as a main component:

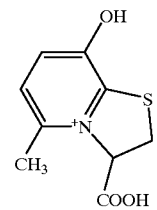

4 Claims, 4 Drawing Sheets

DIAGNOSTIC REAGENT FOR COMPLICATIONS ASSOCIATED WITH DIABETES OR RENAL FAILURE

This application is a continuation of application of International Application PCT/JP98/03190 filed Jul. 16, 1998.

TECHNICAL FIELD

The present invention relates to a diagnostic reagent for complications associated with diabetes or renal failure, containing a particular pyridinium compound as a main component.

BACKGROUND ART

As well known, in the Mailard reaction between sugars and protein amines, first, sugars and protein amines give rise to non-enzymatic reactions (glycation) to form Schiff bases; the Schiff bases give rise to Amadori rearrangement reactions, whereby early-stage products of Mailard reaction, i.e. ketoamines are formed in a relatively short period; and then, after various steps, late-stage products of Mailard reaction are produced.

Of the early-stage products of Mailard reaction, glycated hemoglobin (HbAlc) and glycated albumin (fructosamine) are clinically utilized as an indication for control of blood sugar.

Meanwhile, the late-stage products of Mailard reaction are known to be produced from proteins of slow metabolic turnover in-vivo, such as collagen, myeline, lens and the like and increase in a prolonged high blood sugar condition (diabetes). In order to explain why the persistent high blood sugar condition, which is the most characteristic change in diabetes, gives rise to specific chronic complications to diabetes, attention is being paid to the late-stage products of Mailard reaction which may be a cause for the above phenomenon; and it has been suggested that the hindrance of production of late-stage products of Mailard reaction may prevent the outbreak and development of the complications.

Also, it is expected that the measurement of the concentration of late-stage products of Mailard reaction in blood, urine or tissue may allow a way to make a diagnosis of the above-mentioned complications.

As the components of late-stage products of Mailard reaction, pyrralin, pentosidine and crossline etc. are reported. Of these, pyrraline was separated from the reaction product between neopentylamine and glucose and its structure was determined. Pyrraline is reported to increase in the blood of diabetes patient. However, pyrraline has no fluorescence and is said to be not an important late-stage product of Mailard reaction.

Pentosidine was separated from a reaction product of lysine, arginine and ribose and its structure was determined. Its concentration is high in the skin collagen of diabetes or renal failure patient and significantly high particularly in the blood of renal failure patient. However, pentosidine contributes to only 1% or less of the total crosslinking between proteins in late-stage products of Mailard reaction and is said to be questionable as an important late-stage product of Mailard reaction.

Crossline was separated from the reaction product between acetyllysine and glucose and its structure was determined. However, its association with diabetes is not clarified yet.

Thus, the findings obtained by the so-far developed test methods for late-stage products of Mailard reaction strongly suggest that there are close relations between the increase of later-stage products of Mailard reaction in-vivo and various tissue disorders. However, the chemical structure of an important late-stage product of Mailard reaction in-vivo is unknown.

In view of the above-mentioned situation of the prior art, the present invention has an object of specifying the structure of a late-stage product of Mailard reaction in-vivo which has a close relation with various tissue disorders and also providing a diagnostic reagent for complications associated with diabetes or renal failure, containing the above compound as a main component.

DISCLOSURE OF THE INVENTION

In order to achieve the above object, the present invention provides a diagnostic reagent for complications associated with diabetes or renal failure, containing a pyridinium compound represented by the following formula as a main component:

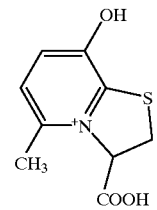

The present inventors made an intensive study in order to find a novel important late-stage product of Mailard reaction in-vivo which reflects the change of disease condition. As a result, the present inventors found out a novel fluorescent compound. A further study by the present inventors confirmed that the compound is a pyridinium compound having the above-shown structure. Moreover, it was found out that the pyridinium compound is useful as a diagnostic reagent for complications associated with diabetes or renal failure. These have led to the completion of the present invention.

BEST MODE FOR CARRYING OUT THE INVENTION

Figure 1:
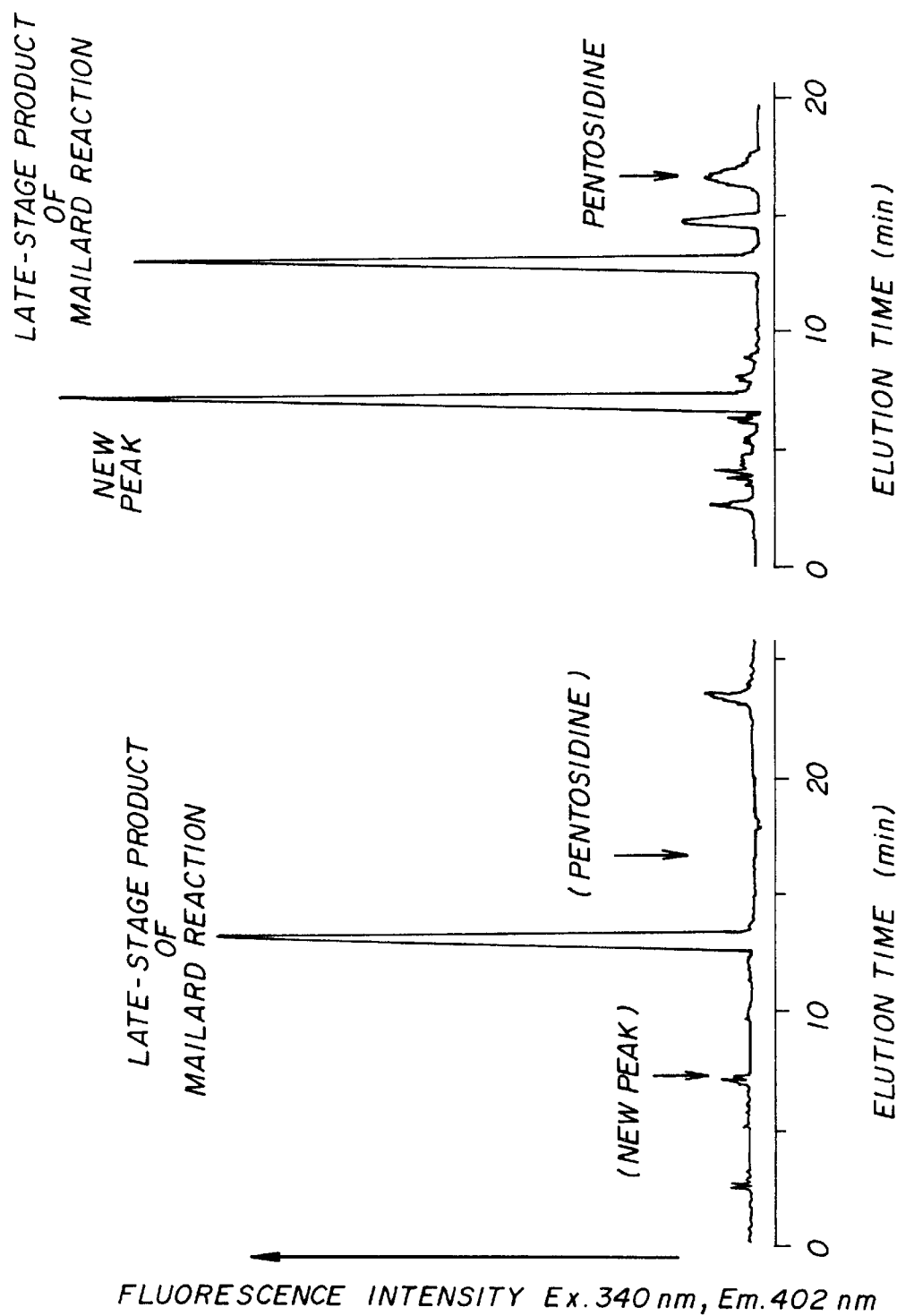
FIG. 1 is a chart showing the result obtained from the analysis of the pyridinium compound of the present invention by high-performance liquid chromatography.

The present invention is described in detail below.

The above pyridinium compound, which is a main component of the present diagnostic reagent for complications, is a kind of a late-stage product of Mailard reaction and is produced by a non-enzymatic reaction between proteins (e.g. albumin, lysozyme, casein, ribonuclease or globulin) and carbonyl compounds (e.g. glucose, diacetyl, glyoxal or fructose).

The above pyridinium compound was detected by reacting rabbit erythrocytes with glucose at 37° C. for 2 weeks, subjecting the reaction mixture to dialysis for 48 hours, hydrolyzing the dialyzate, and then conducting high-performance liquid chromatography using an ODS-5 column at an excitation wavelength of 340 nm and a fluorescence wavelength of 402 nm. The amount of the pyridinium compound produced increased in proportion to the concentration of glucose, the reaction time and the browning of the reaction mixture, and was suppressed by aminoguanidine which is an inhibitor for Mailard reaction. The pyridinium compound was produced similarly also in the reaction system of bovine serum albumin and glucose.

The peak obtained in high-performance liquid chromatography agreed with the peak detected for the blood of diabetes patient.

The structure of the above pyridinium compound was determined as follows. First, the late-stage products of Mailard reaction formed by the reaction of bovine serum albumin with glucose were hydrolyzed; then, the hydrolysis products were separated by high-performance liquid chromatography using a fluorescence wavelength and measured for FAB-mass spectrum using a mixture of glycerol and nitrobenzyl alcohol as a matrix; thereby, the molecular weight of the pyridinium compound was determined to be 212.

With respect to the fluorescence wavelength, the maximum was observed at an excitation wavelength of 350 nm at a fluorescence wavelength of 405 nm.

Next, by measuring the high-resolution mass spectrum, the compositional formula of the pyridinium compound was determined as $C_9H_{10}O_3N_1S_1$. Further, by the containing two-dimension NMR analysis, the pyridinium compound was determined to be 8-hydroxy-5-methyl-dihydrothiazolo[3,2-a]pyridinium-3-carboxylate represented by the following formula:

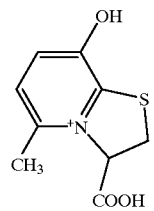

Incidentally, the pyridinium compound was previously isolated from bovine liver as a fluorescent hydrolyzate. Further, the pyridinium compound is presumed to be present in the form of a complex between its precursor and a protein in living bodies.

The present inventors made a reaction of 10 mg/ml of proteins (albumin, globulin, casein, lysozyme, ribonuclease and protamine), with 0.1 M of glucose, and then made subjection the reaction mixture to high-performance liquid chromatography. As a result, it was found that the pyridinium compound was produced in a large amount from albumin ribonuclease (containing arginine and cysteine in large amounts), in a relatively large amount from lysozyme, and in a zero amount from protamine (containing arginine in a large amount but containing no cysteine).

However, addition of cysteine to a combination of protamine and glucose produced the pyridinium compound. Therefore, glucose, a polyarginine and cysteine were found to be necessary for production of the pyridinium compound.

The so-far reported late-stage products of Mailard reaction include, as mentioned above, pyrraline, pentosidine, crossline, etc. Since lysine is associated with production of any of these products, the pyridinium compound is presumed to be a product which has been unknown.

In order to investigate the effect of reducing sugar in production of the pyridinium compound, 10 mg/ml of albumin was reacted with 0.1 M of carbonyl-containing compounds (glucose, diacetyl, glyoxal and fructose) for 2 weeks, and then the reaction mixture was analyzed by high-performance liquid chromatography. As a result, the pyridinium compound was produced even in reaction between albumin and diacetyl and the amount of the pyridinium compound produced was slightly larger than in the reaction between albumin and glucose.

Diacetyl is an acid hydrolysis product of sugar, and reacts specifically with the guanidino group of the arginine residue of protein under a weakly alkaline condition and becomes stable to hydrolysis. Therefore, it is considered that the glucose in solution first undergoes oxidative decomposition and becomes diacetyl, this diacetyl attacks the arginine residue, thereby the pyridinium compound is produced.

The content of the pyridinium compound was significantly low in the serum of experimental diabetes rat administered with streptozotocin but significantly high in the kidney, tendon, skin and nerve of the rat. The amount of the pyridinium compound excreted in urine in the diabetes rat, as compared with that in normal rat, was 4.3-fold per ml of urine, 2.9-fold per protein amount, and 21-fold per day. The amount of the pyridinium compound excreted in urine in hereditarily fat diabetes rat (OLET-F), as compared with that in normal rat (LETO), was 3-fold per protein amount and 22-fold per day.

These facts suggest that the pyridinium compound reflects the advance of condition of diabetes, particularly the reduction of renal function.

The present invention is described in detail as shown below with reference to Examples but is in no way restricted by the Examples.

EXAMPLE 1

10 mg/ml of rabbit erythrocytes and 266 mM of glucose were dissolved in a 10 mM phosphate buffer solution (pH 7.4). The solution was subjected to a reaction at 30° C. for 2 weeks. Protein recovery was made using trichloroacetic acid, and hydrolysis was conducted at 110° C. for 24 hours. The reaction mixture was subjected to high-performance liquid chromatography at an excitation wavelength of 340 nm at a fluorescence wavelength of 402 nm by using an ODS-5 column and pouring 7 mM of phosphoric acid at a rate of 1 ml/min. The analytical result is shown in FIG. 1.

The pyridinium compound of the present invention was detected in 13 minutes (elution time) and a new peak was detected in about 7 minutes. Incidentally, this new peak was formed in a large amount at high temperatures of about 60° C. or under an alkaline condition of pH 9.0 or the like.

EXAMPLE 2

Figure 2:
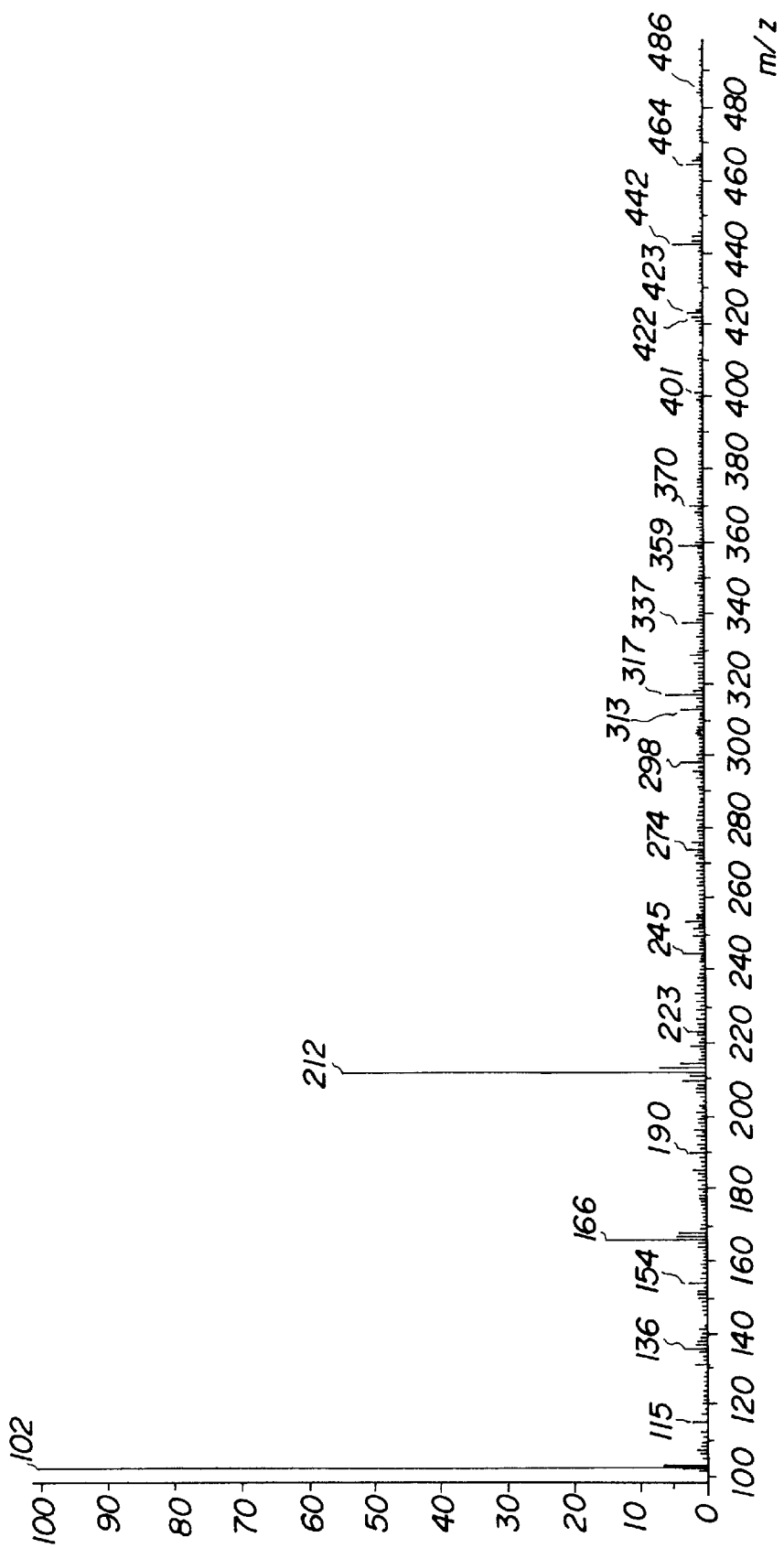
FIG. 2 is a chart showing the result of FAB-mass spectrum measurement for the pyridinium compound of the present invention.

The pyridinium compound formed in a reaction system of bovine serum albumin and glucose was separated by high-performance liquid chromatography, and measured for FAB-mass spectrum using a glycerol-nitrobenzyl alcohol mixture as a matrix. The results are shown in FIG. 2. The pyridinium compound was also measured for high-resolution mass spectrum, and its molecular weight was found to be 212.0404 and the corresponding compositional formula was determined to be $C_9H_{10}O_3NS$ (theoretical value=212.0427).

Figure 3:
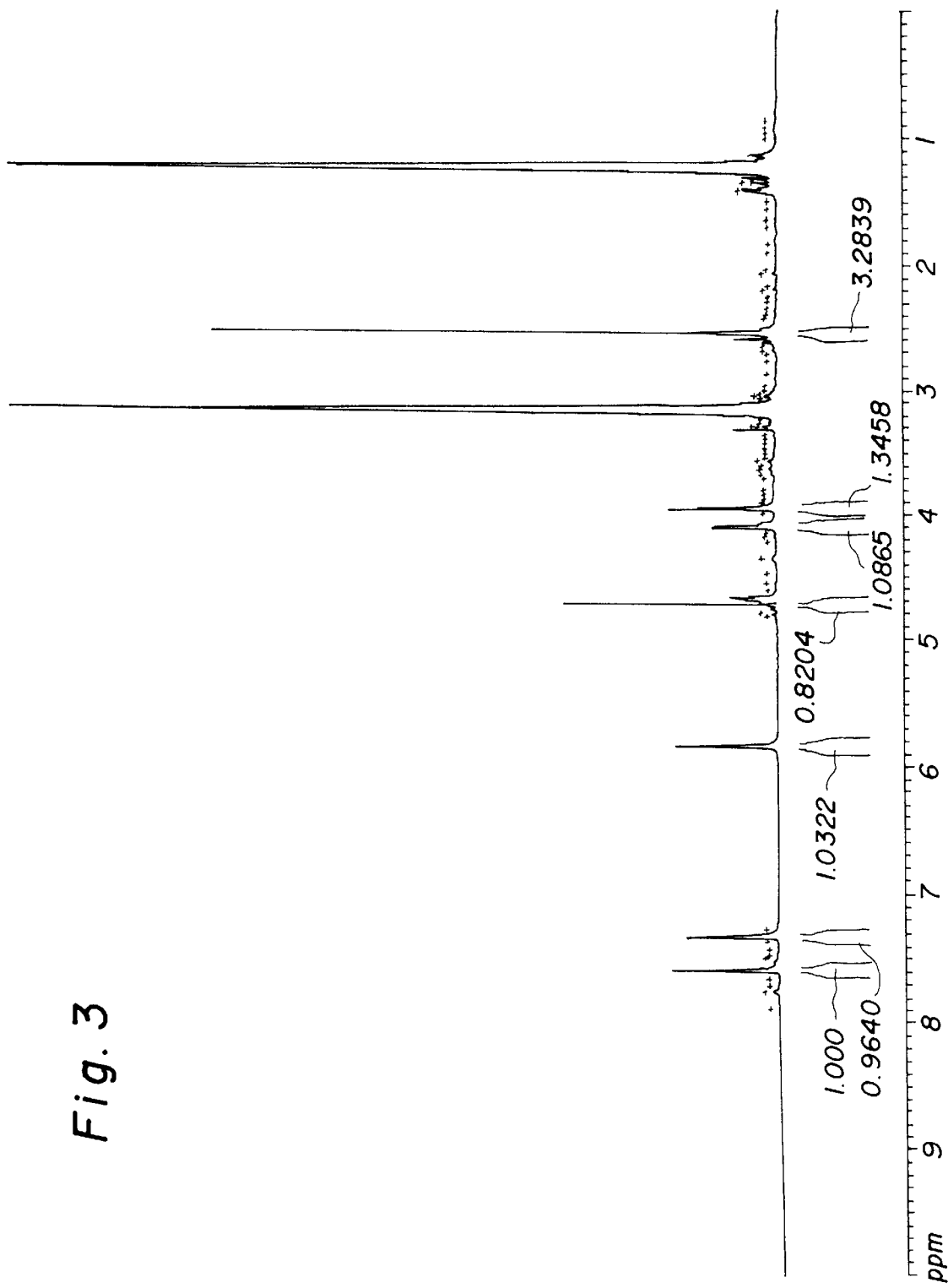
FIG. 3 is a chart showing the result of $^1$H-NMR spectrum measurement for the pyridinium compound of the present invention.
Figure 4:
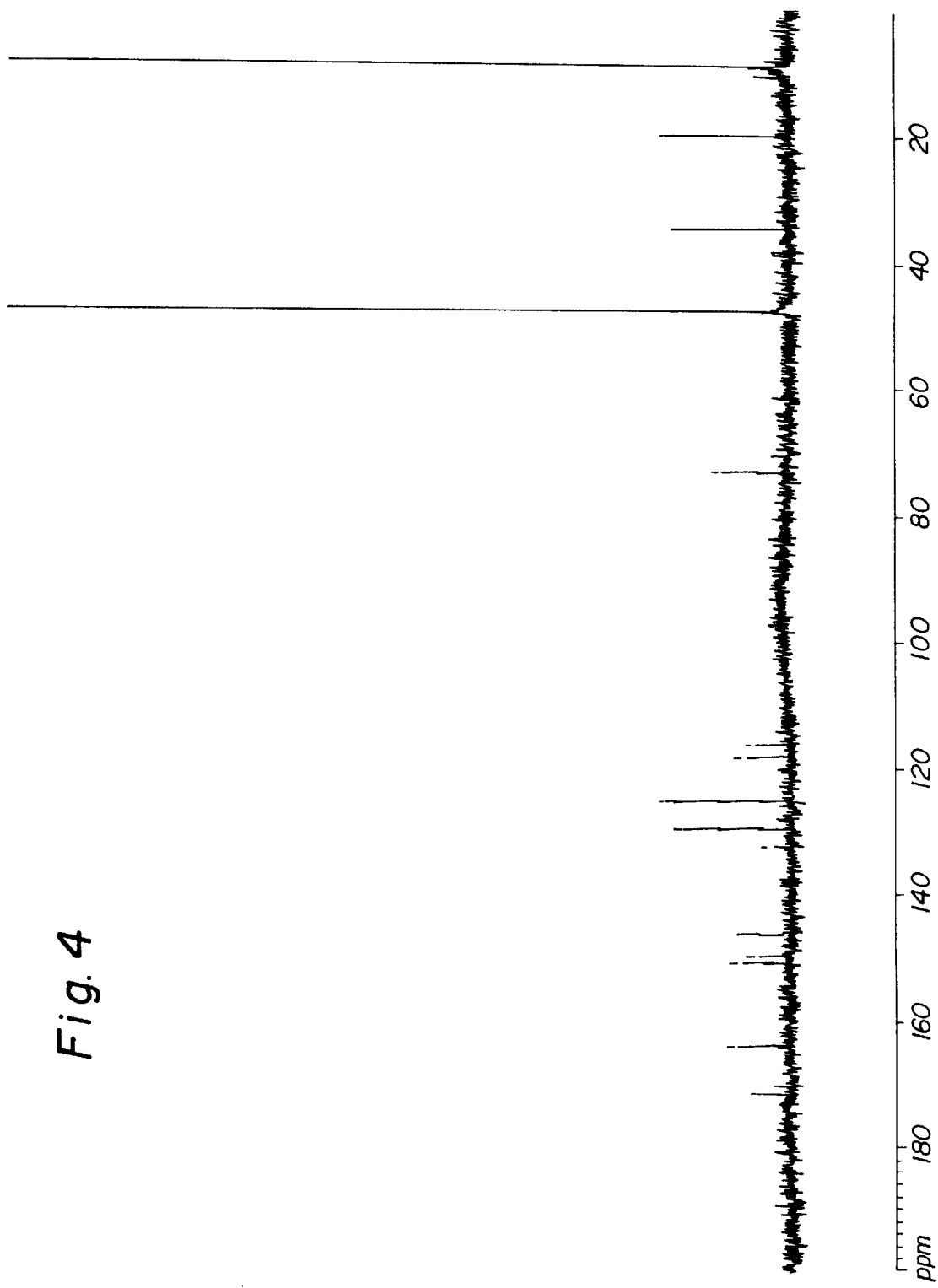
FIG. 4 is a chart showing the result of $^{13}$C-NMR spectrum measurement for the pyridinium compound of the present invention.

The pyridinium compound was dissolved in heavy water and measured for $^1$H-NMR (600 MHz), $^{13}$C-NMR (150 MHz) and HMBC ($^1$H-Detected Heteronuclear Multiple Bond Connectivity). The analytical data are shown in Table 1. Also, the spectrum of $^1$H-NMR is shown in FIG. 3 and the spectrum of $^{13}$C-NMR is shown in FIG. 4.

TABLE 1

Chemical shifts of $^1$H-NMR and $^{13}$C-NMR, and coupling constant of $^1$H-NMR (in $D_2O$, 600 MHz)

|  | C | δ (ppm) | H | δ (ppm) J (Hz) |
|---|---|---|---|---|
| —CH$_3$ | CH$_3$ | 19.9 | 3H | 2.6 s |
| 2 | CH$_2$ | 34.4 | 2H | 3.9 d 11.9 |
|  |  |  |  | 4.1 d, d 11.9, 8.8 |
| 3 | CH | 73.1 | 1H | 5.8 d 8.8 |
| 5 | C | 146.3 |  |  |
| 6 | CH | 125.3 | 1H | 7.4 d 8.4 |
| 7 | CH | 129.5 | 1H | 7.6 d 8.4 |
| 8 | C | 150.6 |  |  |
| 9 | C | 149.6 |  |  |
| —COOH | COOH | 171.1 |  |  |

The methyl group was judged to bond to the aromatic ring because HMBC indicated a correlation between the proton 6 and the proton 3. The protons 2 and the proton 3 showed a typical ABX pattern. That is, one of the protons 2 made geminal coupling of 11.9 Hz by doublet at 3.9 ppm, and the remaining proton 2 made geminal coupling of 11.9 Hz by doublet at 4.1 ppm and also made coupling with the adjacent proton 3 at 8.8 Hz. The proton 3 made coupling with one of the protons 2 by doublet of 8.8 Hz at 5.8 ppm.

From these observation results and $^1$H-$^1$Hcosy, HOHAHA and $^{13}$C-NMR spectroscopic data, the structure of the pyridinium compound used in the present invention was determined to be 8-hydroxy-5-methyldihydrothiazolo[3,2-a]pyridinium-3-carboxylate as shown below.

Incidentally, the correlation by HMBC is shown by arrow marks, in the following structural formula.

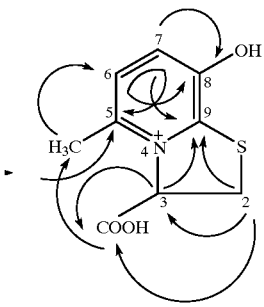

EXAMPLE 3

55 mg/kg of streptozotocin was administered to SD rats from their tail veins to induce diabetes in the rats. The amounts of the pyridinium compound in the organs and urine of each rat were measured and compared with those of normal rats. The results are shown in Table 2.

TABLE 2

Concentrations of pyridinium compound in serum, urine and organs

|  | Normal rats | Diabetes rats |
|---|---|---|
| Serum (mV · sec/ml) | 127 | 84.5*** |
| Tendon (mV · sec/g tissue) | 14.3 | 314*** |
| Skin (mV · sec/g tissue) | 117 | 967*** |
| Urine |  |  |
| ($\mu$V · sec/ml × 10$^3$) | 28.5 | 122.4*** |
| ($\mu$V · sec/mg protein × 10$^3$) | 31.6 | 92.8*** |
| ($\mu$V · sec/24 hr × 10$^6$) | 5.69 | 120*** |

Average error *** P < 0.001

The concentrations of the pyridinium compound in the diabetes rats, as compared with those in the normal rats, were low in serum but significantly high in tendon, skin and urine. In particular, the concentration in urine was as high as 4.3-fold per 1 ml of urine, 2.9-fold per protein amount, and 21-fold per day.

EXAMPLE 4

Hereditarily fat diabetes rats (OLET-F) were raised for 72 weeks, and measured for the amount of pyridinium compound in urine and observed for the pathological change of kidney tissue. The results of measurement and observation were compared with those of normal rats (LETO). The results are shown in Table 3.

TABLE 3

| | Amount of pyridinium compound in urine | | | | | |
|---|---|---|---|---|---|---|
| | 36 weeks | | 48 weeks | | 60 weeks | |
| | /24 hours | /mg protein | /24 hours | /mg protein | /24 hours | /mg protein |
| LETO | 28 ± 3 | 0.91 ± 0.28 | 49 ± 9 | 1.8 ± 0.5 | 19 ± 4 | 0.59 ± 0.2 |
| OLET-F | 650 ± 96** | 5.1 ± 0.39** | 1072 ± 92** | 5.0 ± 0.2** | 2260 ± 298** | 9.7 ± 0.8** |

Average error ** $P < 0.01$

The amounts of the pyridinium compound in the urines of OLET-F, as compared with those of LETO, were 23-fold (36-week age), 22-fold (48-week age) and 16.4-fold (60-week age) per 24 hours, and 5.7-fold (36-week age), 2.8-fold (48-week age) and 16.4-fold (60-week age) per mg of protein; and increased significantly both per 24 hours and per mg of protein with the advance of diabetes.

In the investigation of the pathological change of kidney tissue, the kidneys of OLET-F showed the generation and sclerosis of glomerulus, the atrophy of renal tubule, the cellular infiltration into intercellular space, the thickening of renal pyelic mucosa, etc. With the advance of renal disease, the amount of pyridinium compound excreted into urine increased.

EXAMPLE 5

The amount of pyridinium compound in urine was measured for hereditarily fat diabetes rats (OLET-F) and normal rats (LETO) both of 36-week age, 48-week age or 60-week age. The results are shown in Table 4. Incidentally, the unit used is mv/sec/mg of urinary creatinine.

TABLE 4

| | Concentration of pyridinium compound in urine | | |
|---|---|---|---|
| | 36-week age | 48-week age | 60-week age |
| LETO | 1.63 ± 0.18 | 2.51 ± 0.78 | 1.27 ± 0.10 |
| OLET-F | 34.2 ± 4.11** | 62.0 ± 5.48** | 154.6 ± 23.1** |

Mean ± standard error ** $P < 0.01$

In OLET-F, the amounts of pyridinium compound in urine increased significantly with an increase in age. That is, the amounts in OLET-F, as compared with those in LETO, were as high as 21.0-fold (36-week age), 24.7-fold (48-week age) and 122-fold (60-week age).

EXAMPLE 6

In the kidneys of OLET-F were seen the generation and sclerosis of glomerulus, the atrophy of renal tubule, the cellular infiltration into intercellular space, the thickening of renal pyelic mucosa, etc. These pathological changes of kidney tissues were formularized and examined for correlation with the concentration (mv/sec/mg of creatinine) of pyridinium in urine. As a result, there was seen, between the two, a significant correlation of γ (correlation coefficient)= 0.6485. The concentration of pyridinium compound in urine had also a significant correlation of γ=−0.6721 with creatinine clearance. Thus, it has become clear that the concentration of pyridinium compound in urine reflects the change of renal function.

EXAMPLE 7

By measuring the amounts of pyridinium compound in the urines of OLET-F or LETO of 36-week age, 48-week age or 60-week age, and examining correlation of these amounts with the score of histological change of kidney tissue, creatinine clearance and turbidity of eye lens at 72-week age (time of slaughter), the present inventors investigated whether or not the amount of pyridinium compound in urine could be utilized for diagnosis (prognosis) of pathema. The results are shown in Table 5.

TABLE 5

| | Diagnosis and prognosis by pyridinium compound in urine (correlation efficient) | | | | | |
|---|---|---|---|---|---|---|
| | Score of kidney change | | Creatinine clearance | | Turbidity of eye lens | |
| | Pyridinium compound | Fructosamine | Pyridinium Compound | Fructosamine | Pyridinium compound | Fructosamine |
| 36 weeks | 0.6479 | 0.2730 | −0.6794 | −0.2195 | 0.6030 | 0.6064 |
| 48 weeks | 0.6672 | 0.4516 | −0.5306 | −0.3873 | 0.4869 | 0.8377 |
| 60 weeks | 0.6443 | 0.2208 | −0.6721 | −0.1719 | 0.6568 | 0.7880 |

The pyridinium compound and fructosamine were compared as to their applicability to diagnosis and prognosis. As a result, the concentration of pyridinium compound in urine was found to be able to diagnose and prognose, at a timing of 36 weeks before slaughter, the outbreak of diabetic complications such as reduction in creatinine clearance, histological change of kidney tissue, turbidity of eye lens and the like.

EXAMPLE 8

Pyridinium compound in urine was measured for patients of chronic renal failure and healthy persons, and their correlations with the urinary protein concentration (utilized as a marker indicating the change of renal function) were investigated. The results are shown in Table 6.

TABLE 6

Concentrations of pyridinium compound and protein in urines of patients of renal failure

| | Number of Testees | Pyridinium compound in urine × $10^4$ area/mg of creatinine | Protein in urine mg/dl |
|---|---|---|---|
| Healthy persons | 16 | 292 ± 51 | 5.37 ± 1.02 |
| Patients of chronic renal failure | 25 | 1053 ± 267 | 131.0 ± 27.6 |
| | | ** | ** |

Mean ± standard error **P < 0.01

The concentrations of pyridinium compound in urines of patients of renal failure were 3.6-fold and the concentrations of protein in their urines were 24.4-fold, as compared with those in healthy persons. The correlation coefficient of the two was significantly high at γ=0.8709, and the pyridinium compound in urine was found to be useful as a marker for renal function.

INDUSTRIAL APPLICABILITY

The pyridinium compound represented by the following formula:

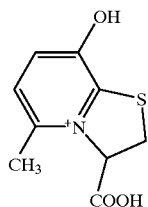

is produced in a large amount in diabetes, deposits on the tissues of kidney, tendon, skin, nerve, etc., and is excreted in a large amount in urine with the reduction in renal function. Therefore, the pyridinium compound can be used as a biomarker for diabetes. The diagnostic reagent of the present invention for complications associated with diabetes or renal failure contains the above pyridinium compound as a main component.

What is claimed is:

1. A method for detecting pyridinium as a marker for diabetes or renal failure in a mammal having diabetes or renal failure, comprising detecting in urine obtained from said mammal a concentration of a pyridinium compound of the formula:

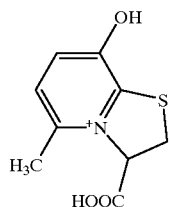

wherein the concentration of the pyridinium compound correlates with diabetes or renal failure.

2. A method for the determination of the presence of diabetes or renal failure in a mammal having diabetes or renal failure comprising quantifying the concentration of a pyridinium compound of the formula:

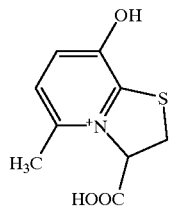

in a urine sample obtained from said mammal and comparing with the corresponding concentration of said pyridinium compound in a normal urine sample, whereby an elevated concentration of said pyridinium compound is indicative of the presence of diabetes or renal failure in said mammal.

3. A diagnostic kit for determining the concentration of a pyridinium compound of the formula:

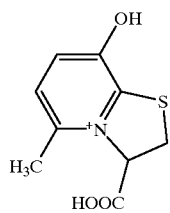

comprising a standard marker which comprises at least one known concentration of said pyridinium compound, wherein said marker is used as a standard for a quantitative analysis method.

4. The diagnostic kit according to claim 3 wherein said quantitative analysis method is high performance liquid chromatography (HPLC).

* * * * *